United States Patent
Den Hartog et al.

(10) Patent No.: US 7,307,079 B2
(45) Date of Patent: Dec. 11, 2007

(54) 1,3,5-TRIAZINE DERIVATIVES AS LIGANDS FOR HUMAN ADENOSINE-A3 RECEPTORS

(75) Inventors: Jacobus A.J. Den Hartog, Weesp (NL); Jan H. Reinders, Weesp (NL); Guustaaf J.M. Van Scharrenburg, Weesp (NL); Maria L. Pras-Raves, Weesp (NL); Gary R. Gustafson, Bedford, MA (US)

(73) Assignees: Solvay Pharmaceuticals, B.V., Weesp (NL); Arqule, Inc., Woburn, MA (US)

( * ) Notice: Subject to any disclaimer, the term of this patent is extended or adjusted under 35 U.S.C. 154(b) by 156 days.

(21) Appl. No.: 10/448,024

(22) Filed: May 30, 2003

(65) Prior Publication Data

US 2004/0038972 A1    Feb. 26, 2004

(30) Foreign Application Priority Data

May 30, 2002  (EP)  ............................... 02077310.7
May 30, 2002  (NL)  .................................. 1020725

(51) Int. Cl.
| | |
|---|---|
| C07D 251/46 | (2006.01) |
| C07D 251/52 | (2006.01) |
| C07D 251/54 | (2006.01) |
| C07D 401/04 | (2006.01) |
| C07D 401/14 | (2006.01) |
| C07D 403/04 | (2006.01) |
| C07D 403/14 | (2006.01) |
| A61K 31/53 | (2006.01) |
| A61K 31/4025 | (2006.01) |
| A61K 31/4523 | (2006.01) |
| A61P 11/06 | (2006.01) |
| A61P 17/06 | (2006.01) |
| A61P 25/26 | (2006.01) |
| A81P 19/02 | (2006.01) |

(52) U.S. Cl. ............... 514/245; 514/241; 514/217.05; 544/197; 544/198; 544/207; 544/208; 544/209; 544/219; 540/480; 540/596

(58) Field of Classification Search ............... 544/197, 544/198, 206, 207, 208, 209, 219; 514/241, 514/245, 217.05; 540/480, 598, 596
See application file for complete search history.

(56) References Cited

U.S. PATENT DOCUMENTS 5,885,993 A *    3/1999    Ueda .................... 514/245
2004/0077648 A1 *   4/2004    Timmer et al. ............ 514/241

FOREIGN PATENT DOCUMENTS

WO    WO 99/11633 A1    3/1999
WO    WO-2004/026844 A1 *    4/2004

OTHER PUBLICATIONS

Baraldi et al., European Journal of Medicinal Chemistry 38: 367-382, 2003.*
Gao et al. Curr. Top. Med. Chem. 4(8): 855-862, 2004.*
CA Abstract CA 140:303704, 2004.*
English language Derwent abstract of WO 99/11633 A1, Mar. 11, 1999.

* cited by examiner

Primary Examiner—Venkataraman Balasubramanian
(74) Attorney, Agent, or Firm—Finnegan, Henderson, Farabow, Garrett & Dunner L.L.P.

(57) ABSTRACT

The invention relates to a group of novel triazine derivatives which are ligands for human adenosine-$A_3$ receptors, as well as to pharmaceutical compositions containing a pharmacologically active amount of at least one of these compounds as an active ingredient. The invention relates to compounds of the general formula (1)

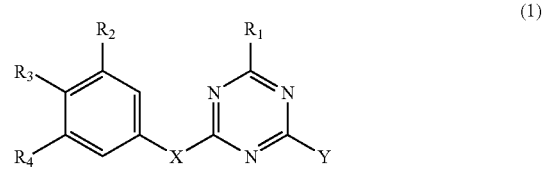

(1)

wherein Y represents a group of the general formula (A), (B) or (C)

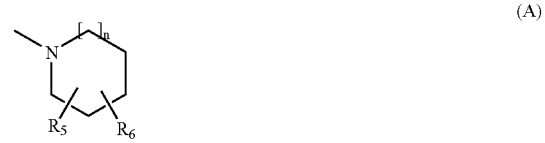

(A)

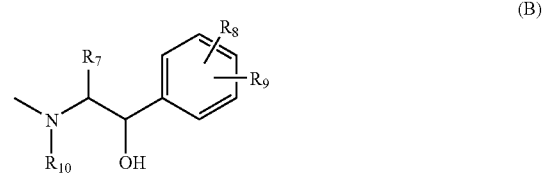

(B)

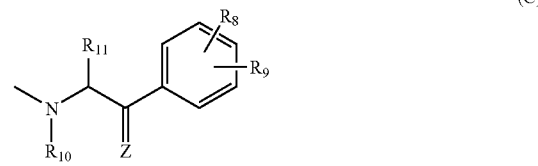

(C)

and all other symbols have the meanings as given in the description.

14 Claims, No Drawings

1,3,5-TRIAZINE DERIVATIVES AS LIGANDS FOR HUMAN ADENOSINE-A3 RECEPTORS

This application claims priority to European Patent Application Number 02077310.7, filed May 30, 2002 and The Netherlands Patent Application Number NL 1020725, filed May 30, 2002, the contents of which are incorporated herein by reference.

The present invention relates to a group of novel triazine derivatives which are ligands for human adenosine-$A_3$ receptors. The invention also relates to pharmaceutical compositions containing a pharmacologically active amount of at least one of these novel triazine derivatives as an active ingredient.

Caffeine and theophylline, two well known natural compounds, exert their pharmacological activities by interacting with adenosine receptors. This discovery had a major impact on adenosine receptor research. At present, four types of adenosine receptors have been identified and designated $A_1$, $A_{2A}$, $A_{2B}$ and $A_3$ respectively. All four belong to the superfamily of seven transmembrane G-protein coupled receptors. Adenosine receptors are ubiquitous and involved in a great variety of biological processes. Thus, during the past decades the therapeutic potential of adenosine receptor ligands has resulted in a substantial research interest. Recent reviews are: S. Hess, Recent advances in adenosine receptor antagonist research, Expert Opin. Ther. Patents, 11, 1547-1562, 2001, and M. A. Jacobson, Adenosine receptor agonists, Expert Opin. Ther. Patents, 12(4), 489-501, 2002.

Ligands for the various adenosine receptors are the subject of a large number of patent applications and patents. In only two of those triazines are described. WO 991163 describes a series of 2,4-bisphenyl substituted triazines showing nanomolar affinity for human adenosine-$A_1$ receptors.

The second patent application describing triazines, JP 11158073, describes a series of substituted 1,3,5-triazines which are ligands for human adenosine-$A_3$ receptors, the most potent of which having affinities around 15 nM.

Surprisingly, it has now been found that in a series of triazine derivatives with novel combinations of substituents, a group of compounds was shown to have an affinity for human adenosine-$A_3$ receptors in the low nanomolar range.

The invention relates to compounds of the general formula (1)

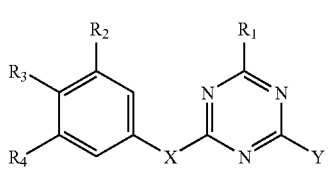

(1)

wherein:

$R_1$ represents halogen, alkyl(1-3C), O-alkyl(1-3C), $CF_3$, $NH_2$, N-(di)-alkyl(1-3C), N-(di)-alkenyl(1-3C), N-(di)-alkynyl(1-3C), N-alkyl(1-3C)alkenyl(1-3C), N-alkyl(1-3C)alkynyl(1-3C), N-alkenyl(1-3C)alkynyl(1-3C) or an optionally substituted $C_2$-$C_8$ cycloalkylamino group, $R_2$, $R_3$ and $R_4$ independently represent H, halogen, alkyl(1-3C), $CF_3$, OH, O-alkyl(1-3C), phenoxy, hydroxyalkyl(1-3C), alkoxy(1-2C)-alkyl(1-2C), phenyl, N-(di)-alkyl(1-3C), 1-morpholinyl, 1-piperidinyl, 1-piperazinyl, $OCF_3$, $SCH_3$, $SOCH_3$, $SO_2CH_3$ or $R_2$ and $R_3$ together with the phenyl ring to which they are attached, represent an optionally substituted benzofuran, dihydrobenzofuran, benzodioxane, benzodioxolane or naphthalene ring system, X represents NH, N-alkyl(1-3C), $CH_2$, O, S or a carbon-carbon bond, Y represents a group of the general formula (A), (B) or (C):

(A)

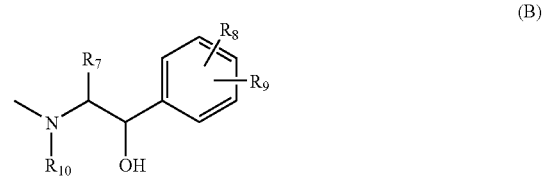

(B)

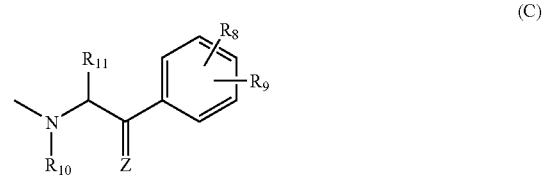

(C)

in which:

$R_5$ is either OH or $CH_2OH$ $R_6$ represents H, alkyl(1-3C), phenyl, $NH_2$, N-(di)-alkyl(1-3C), OH, O-alkyl(1-3C) or hydroxyalkyl(1-2C);

n has the value of 0, 1 or 2;

$R_7$ represents alkyl(1-3C), benzyl, hydroxyalkyl(1-2C) or methoxyalkyl(1-2C), $R_8$ and $R_9$ independently represent H, halogen, alkyl(1-3C), $CF_3$, OH, O-alkyl(1-3C), N-(di)-alkyl(1-3C), 1-morpholinyl, 1-piperidinyl, 1-piperazinyl, $OCF_3$, $SCH_3$, $SOCH_3$, or $SO_2CH_3$, $R_{10}$ represents H or alkyl(1-3C), $R_{11}$ represents H, alkyl(1-3C), benzyl, hydroxyalkyl(1-2C) or methoxyalkyl(1-2C), Z represents NOH, NOalkyl(1-3C), O or S, and pharmacologically acceptable salts thereof.

In the description of the substituents the abbreviation 'alkyl(1-3C)' means 'methyl, ethyl, n-propyl or isopropyl'.

In this specification '$C_2$-$C_8$ cycloalkylamino' means any cyclic amine containing from 2 to 8 carbons in the ring. The cycloalkylamino ring may contain other atoms and may be optionally substituted. Examples of $C_2$-$C_8$ cycloalkylamino include pyrrolidinyl, piperidinyl, morpholinyl, aziridinyl, pyrrolinyl and the like.

In this specification 'optionally substituted' means that a group may or may not be further substituted by one or more groups selected from alkyl, alkenyl, alkynyl, aryl, fluoro, chloro, bromo, hydroxyl, alkyloxy, alkenyloxy, aryloxy, acyloxy, amino, alkylamino, dialkylamino, arylamino, thio, alkylthio, arylthio, cyano, oxo, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulphur. Optional substituents may themselves bear additional optional substituents. Preferred optional substituents include $C_{1-3}$ alkyl such as for example methyl, ethyl, and trifluoromethyl, fluoro, chloro, bromo, hydroxyl, $C_{1-3}$ alkyloxy such as for example methoxy, ethoxy and trifluoromethoxy, and amino.

All compounds having formula (1) in which the substituents on asymmetrical carbon atoms are in either the R-configuration or the S-configuration belong to the invention.

Also prodrugs, i.e. compounds which when administered to humans by any known route, are metabolized to compounds having formula (1), belong to the invention. In particular this relates to compounds with primary or secondary amino groups or hydroxy groups, a typical example being the compound with formula (9) and its enantiomers (see below). Such compounds can be reacted with organic acids to yield compounds which can be metabolized to compounds having formula (1).

The invention particularly relates to compounds having formula (1) wherein $R_1$ represents halogen, alkyl(1-3C), O-alkyl(1-3C), $CF_3$, $NH_2$ or N-(di)-alkyl(1-3C), and all other symbols have the meanings as given above.

More particular the invention relates to compounds having formula (1) wherein $R_1$=Cl, $R_2$=H, X=NH, Y is either group (A), (B) or (C), $R_6$=H, n=1, Z=O, $R_{10}$=H and $R_3$, $R_4$, $R_5$, $R_7$, $R_8$, $R_9$ and $R_{11}$ have the meanings as described above, and including all possible stereo-isomers and prodrugs as outlined above, thus as represented by the general formulas (2), (3) and (4):

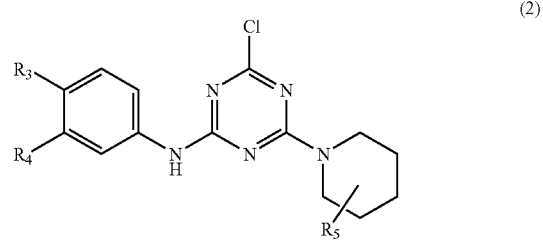

(2)

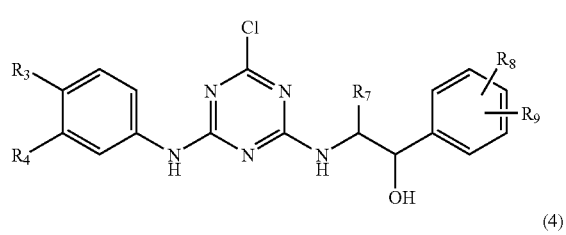

(3)

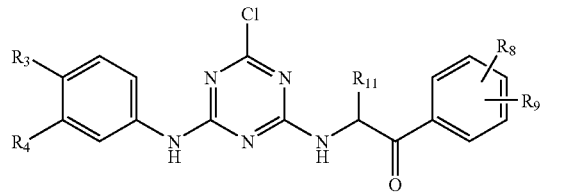

(4)

Yet more particular the invention relates to compounds of either formula (2), (3) or (4) in which $R_5$=3—$CH_2OH$; $R_7$=$CH_3$; $R_8$=H; $R_9$=H; $R_{11}$=$CH_3$ and $R_3$ and $R_4$ have the meanings as described above, and including all possible stereo-isomers and prodrugs as outlined above, thus as represented by the general formulas (5), (6) and (7):

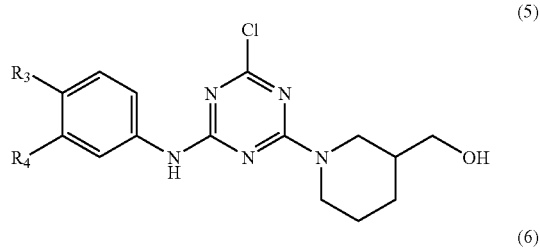

(5)

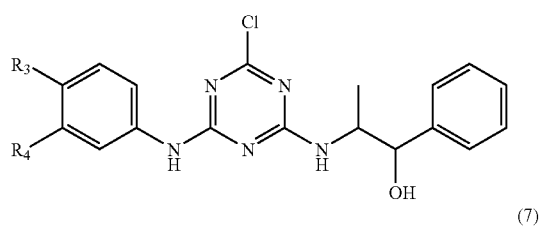

(6)

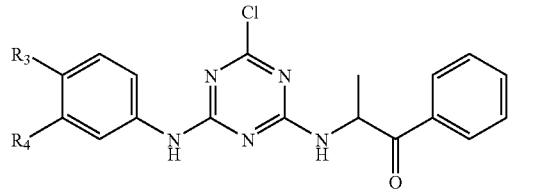

(7)

Even more preferred is the compound having formula (8) and its enantiomers.

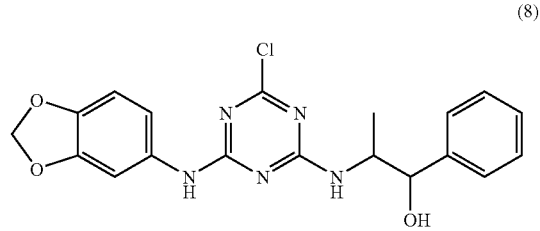

(8)

The best mode of the invention is the compound represented by formula (9):

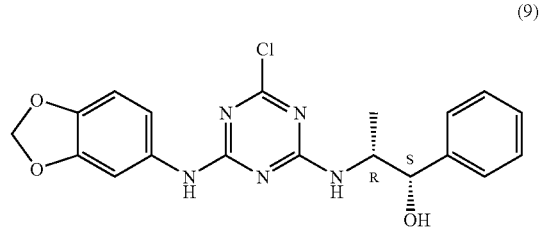

(9)

This compound has an affinity for human adenosine-$A_3$ receptors of $pK_i 9.0 \pm 0.3$.

The compounds of the invention and their salts can be obtained according to the general routes outlined below. Those with $R_1$=Cl are synthesized according to scheme 1:

scheme 1

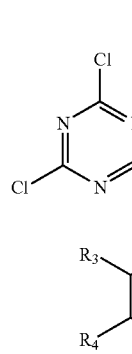
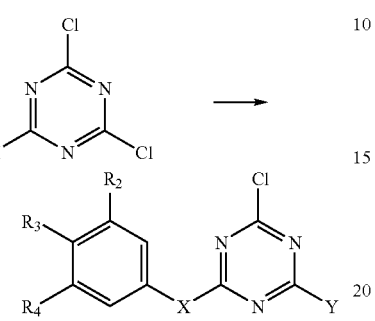

Experimental details for the first step in this general route are given in:
J. Amer. Chem. Soc. 116, 1994, 4326 for X=NH;
Chem. Pharm. Bull. 45, 1997, 291 for X=N-alkyl;
Tetrahedron 56, 2000, 9705 for X=CH$_2$;
Pol. J. Chem. 74, 2000, 837 for X=O;
J Chem. Soc. C 1967, 466 for X=S, and in
Tetrahedron 56, 2000, 9705 for X=carbon-carbon bond.

The disclosure of these documents is specifically incorporated herein by reference.

The compounds of the invention with R$_1$=F or Br can be obtained fully analogously from the corresponding tri-halo derivatives. Experimental details are given in:
J. Med Chem. 36 (26), 4195-4200, 1993 for R$_1$ is F, and in
J. Prakt. Chem. 82, 536, 1910 for R$_1$=Br.

The disclosure of these documents is specifically incorporated herein by reference.

The compounds of the invention with R$_1$=O-alkyl(1-3C) or any of the amine substituents: NH$_2$, N-(di)-alkyl(1-3C), N-(di)-alkenyl(1-3C), N-(di)-alkynyl(1-3C), N-alkyl(1-3C) alkenyl(1-3C), N-alkyl(1-3C) alkynyl(1-3C), N-alkenyl(1-3C)alkynyl(1-3C) or an optionally substituted C$_2$-C$_8$ cycloalkylamino group, can be obtained by further substitution of the chloro-derivatives as outlined below in scheme 2:

scheme 2

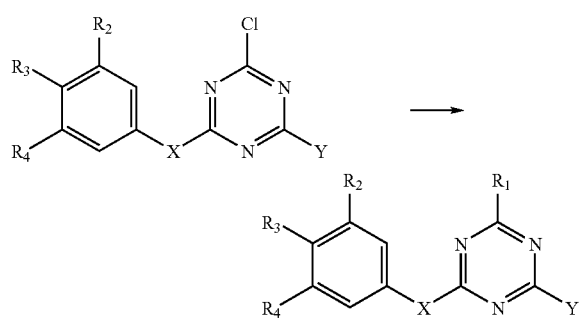

Experimental details are given in:
Heterocycles 31 (5), 895-909, 1990 for R$_1$=alkoxy, and in
Tetrahedron, 54 (1998) 4051-4065 for R$_1$=(substituted) amine.

The disclosure of these documents is specifically incorporated herein by reference.

Compounds of the invention with R$_1$=alkyl(1-3C), CF$_3$ or iodine can be obtained by following the sequence of synthetic steps outlined below in Scheme 3.

Scheme 3

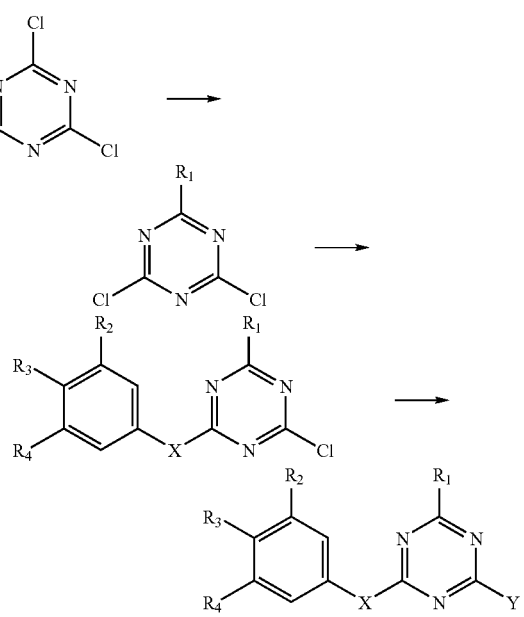

Experimental details are given in:
J. Med Chem 42 (5), 805-818, 1999 for R$_1$=alkyl,
J. Chem Soc., Chem Comm 1988, (10) 638-639 for R$_1$=CF$_3$, and in
Eur. J. Org. Chem., 2002, 4181-4184 for R$_1$=iodine The disclosure of these documents is specifically incorporated herein by reference.

Pharmaceutically acceptable salts may be obtained using standard procedures well known in the art, for example by mixing a compound of the present invention with a suitable acid.

Suitable acid addition salts can be formed with inorganic acids such as hydrochloric acid, sulphuric acid, phosphoric acid and nitric acid, or with organic acids such as citric acid, fumaric acid, maleic acid, tartaric acid, acetic acid, trifluoro acetic acid, benzoic acid, p-toluene sulphonic acid, methanesulphonic acid and naphthalene sulphonic acid.

The compounds of the invention of the general formula (1), as well as the salts thereof, have adenosine-A$_3$ (ant) agonistic activity. They are useful in the treatment of disorders in which adenosine-A$_3$ receptors are involved, or that can be treated via manipulation of those receptors. For instance in: acute and chronic pain, inflammatory diseases including, arthritis, multiple sclerosis, asthma and psoriasis; gastro-intestinal disorders such as ulcers, inflammatory bowel disease (Crohn's disease) and ulcerative colitis; allergic responses such as eczema, atopic dermatitis and rhinitis; cardio-vascular disorders such as myocardial infarction, arrhythmias, hypertension, thrombosis, anaemia, arteriosclerosis, angina pectoris, cutaneous diseases such as urticaria, lupus erythematosus and pruritus; opthalmological disorders like glaucoma; respiratory disorders including chronic obstructive pulmonary disease, bronchitis and cystic fibrosis; central nervous system disorders including various forms of epilepsy, stroke, depression, sleep apnoea; disorders characterized by impairment of cognition and memory such as Alzheimer's disease, Creutzfeldt-Jacob disease, Huntington's disease, Parkinson's disease, neurorehabilitation (post-traumatic brain lesions); acute brain or spinal cord injury; diabetes, osteoporosis, diseases of the immune system, various carcinomas and leukemia, bacterial and viral infections.

The adenosine-$A_3$ receptor (ant)agonistic properties of the compounds of the invention were determined using the method outlined below.

Receptor Binding to Human Adenosine-$A_3$ Receptors

Affinity of the compounds for human adenosine-$A_3$ receptors was determined using the receptor binding assay described by C. A. Salvatore et al.: Molecular cloning and characterization of the human $A_3$ adenosine receptor, Proc. Natl. Acad. Sci. USA, 90, 10365-10369, 1993. Briefly, membrane preparations were obtained from human recombinant (HEK 293) cells in which the human adenosine-$A_3$ receptor was stably expressed. Membranes were incubated at 22° C. for 90 minutes with [$^{125}$I]-AB-MECA in the absence or presence of testcompounds in a concentration range from 10 μM down to 0.1 nM, diluted in a suitable buffer. Separation of bound radioactivity from free was done by filtration through Packard GF/B glass fiber filters with several washings with ice-cold buffer using a Packard cell harvester. Bound radioactivity was measured with a scintillation counter (Topcount, Packard) using a liquid scintillation cocktail (Microscint 0, Packard). Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_I$ values were calculated by correcting the $IC_{50}$ values for radioligand concentration and its affinity for the human adenosine-$A_3$ receptor according to the Cheng-Prusoff equation:

$$pK_I = -\log(IC_{50}/(1+S/K_d))$$

in which the $IC_{50}$ is as described above, S is the concentration [$^{125}$I]-AB-MECA used in the assay expressed in mol/l (typically 0.1 nM), and $K_d$ is the equilibrium dissociation constant of [$^{125}$I]-AB-MECA for human adenosine-$A_3$ receptors (0.22 nM).

The compounds of the invention have a high affinity for adenosine-$A_3$ receptors in the binding assay described above. This property makes them useful in the treatment of disorders in which adenosine-$A_3$ receptors are involved, or that can be treated via manipulation of these receptors.

EXAMPLES (1S,2R)-2-{[4-chloro-6-(3,4-methylenedioxy-phenylamino)-[1,3,5]triazin-2-yl]-amino}-1-phenyl-propan-1-ol To a solution of cyanuric chloride (1.84 gr) in acetonitrile (20 ml), kept at a temperature of −20° C. under stirring, dropwise were subsequently added solutions of 3,4-methylenedioxy-aniline (1.37 gr) in acetonitrile (20 ml) and diisopropylethylamine (DIPEA) (1.29 gr) in acetonitrile (20 ml). After stirring at −20° C. for 1 hour, again dropwise were subsequently added solutions of DIPEA (1.29 gr) in acetonitrile (20 ml) and (1 S,2R)-(+)-norephedrine (1.51 gr) in acetonitrile (20 ml). The mixture was allowed to warm to room temperature and was stirred for another 2 hours. The resulting reaction mixture was concentrated in vacuo. After addition of ethylacetate (250 ml) the organic layer was subsequently washed with a solution of HCl in water (1M, 100 ml), a solution of NaOH in water (1 M, 100 ml) and brine (50 ml). The organic layer was dried over sodiumsulphate, filtered and concentrated in vacuo. The resulting product was purified by column chromatography using silicagel and a mixture of heptane: ethylacetate (3:1) as the eluent. The resulting pure product (formula (9), see above, example B-44, see table) was obtained as a white solid in 80% yield.

The invention is further illustrated by means of the following specific examples listed in the tables below and represented by the general formula:

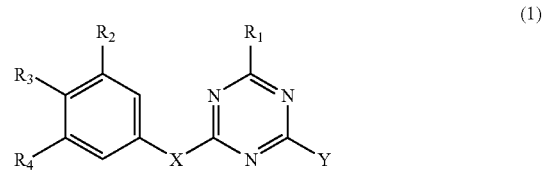

(1)

wherein Y represents a group of the general formula (A), (B) or (C):

(A)

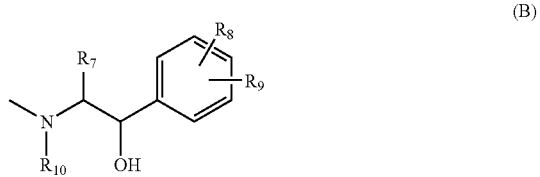

(B)

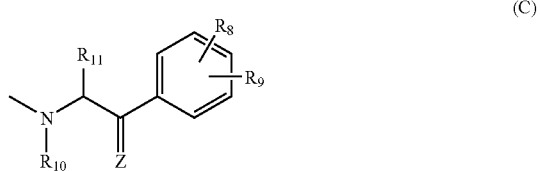

(C)

These examples are only intended to further illustrate the invention in more detail, and therefore are not deemed to restrict the scope of the invention in any way.

| nr | R₁ | X | R₂ | R₃ | R₄ | Y | n | R₅ | R₆ |
|---|---|---|---|---|---|---|---|---|---|
| A-1 | Cl | NH | H | H | H | (A) | 1 | 3-CH₂OH | H |
| A-2 | Cl | NH | OCH₃ | H | H | (A) | 1 | 3-CH₂OH | H |
| A-3 | Cl | NH | OCH₃ | H | H | (A) | 1 | 3-CH₂OH | 4-CH₃ |
| A-4 | Cl | NH | OCH₃ | H | H | (A) | 1 | 3-CH₂OH | 4-phenyl |
| A-5 | Cl | NH | OCH₃ | H | H | (A) | 1 | 3-CH₂OH | 4-N(CH₃)₂ |
| A-6 | Cl | NH | OCH₃ | H | H | (A) | 1 | 3-CH₂OH | 5-CH₂OH |
| A-7 | Cl | NH | H | OCH₃ | H | (A) | 1 | 3-CH₂OH | H |
| A-8 | Cl | NH | CH₃ | H | H | (A) | 1 | 3-CH₂OH | H |
| A-9 | Cl | NH | Cl | H | H | (A) | 1 | 3-CH₂OH | H |
| A-10 | Cl | NH | OC₂H₅ | H | H | (A) | 1 | 3-CH₂OH | H |
| A-11 | Cl | NH | H | OC₂H₅ | H | (A) | 1 | 3-CH₂OH | H |
| A-12 | Cl | NH | CH(OH)CH₃ | H | H | (A) | 1 | 3-CH₂OH | H |
| A-13 | Cl | NH | H | 1-morpholinyl | H | (A) | 1 | 3-CH₂OH | H |
| A-14 | Cl | NH | CH₃ | CH₃ | H | (A) | 1 | 3-CH₂OH | H |
| A-15 | Cl | NH | F | CH₃ | H | (A) | 1 | 3-CH₂OH | H |
| A-16 | Cl | NH | F | OCH₃ | H | (A) | 1 | 3-CH₂OH | H |
| A-17 | Cl | NH | OCH₃ | H | CF₃ | (A) | 1 | 3-CH₂OH | H |
| A-18 | Cl | NH | OCH₃ | H | OCH₃ | (A) | 1 | 3-CH₂OH | H |
| A-19 | Cl | NH | -phenyl- | | H | (A) | 1 | 3-CH₂OH | H |
| A-20 | Cl | NH | —O—CH₂—O— | | H | (A) | 1 | 3-OH | H |
| A-21 | Cl | NH | —O—CH₂—O— | | H | (A) | 1 | 4-OH | H |
| A-22 | Cl | NH | —O—CH₂—O— | | H | (A) | 1 | 4-OH | 4-phenyl |
| A-23 | Cl | NH | H | H | H | (A) | 1 | 4-OH | H |
| A-24 | Cl | NH | H | CH₃ | H | (A) | 1 | 4-OH | H |
| A-25 | Cl | NH | Cl | H | H | (A) | 1 | 4-OH | H |
| A-26 | Cl | NH | OCH₃ | H | H | (A) | 1 | 4-OH | H |
| A-27 | Cl | NH | H | OCH₃ | H | (A) | 1 | 4-OH | H |
| A-28 | Cl | NH | OC₂H₅ | H | H | (A) | 1 | 4-OH | H |
| A-29 | Cl | NH | H | OC₂H₅ | H | (A) | 1 | 4-OH | H |
| A-30 | Cl | NH | H | (CH₂)₂OH | H | (A) | 1 | 4-OH | H |
| A-31 | Cl | NH | O-phenyl | H | H | (A) | 1 | 4-OH | H |
| A-32 | Cl | NH | H | O-phenyl | H | (A) | 1 | 4-OH | H |
| A-33 | Cl | NH | H | 1-morpholinyl | H | (A) | 1 | 4-OH | H |
| A-34 | Cl | NH | CH₃ | CH₃ | H | (A) | 1 | 4-OH | H |
| A-35 | Cl | NH | F | CH₃ | H | (A) | 1 | 4-OH | H |
| A-36 | Cl | NH | F | OCH₃ | H | (A) | 1 | 4-OH | H |
| A-37 | Cl | NH | OCH₃ | H | CF₃ | (A) | 1 | 4-OH | H |
| A-38 | Cl | NH | OCH₃ | H | OCH₃ | (A) | 1 | 4-OH | H |
| A-39 | Cl | NH | -phenyl- | | H | (A) | 1 | 4-OH | H |
| A-40 | Cl | NH | —O—CH₂—O— | | H | (A) | 1 | 2-CH₂OH | H |
| A-41 | Cl | NH | OCH₃ | H | H | (A) | 1 | 2-CH₂OH | H |
| A-42 | Cl | NH | H | OCH₃ | H | (A) | 1 | 2-CH₂OH | H |
| A-43 | Cl | NH | H | OC₂H₅ | H | (A) | 1 | 2-CH₂OH | H |
| A-44 | Cl | NH | H | 1-morpholinyl | H | (A) | 1 | 2-CH₂OH | H |
| A-45 | Cl | NH | CH₃ | CH₃ | H | (A) | 1 | 2-CH₂OH | H |
| A-46 | Cl | NH | F | OCH₃ | H | (A) | 1 | 2-CH₂OH | H |
| A-47 | Cl | NH | OCH₃ | H | OCH₃ | (A) | 1 | 2-CH₂OH | H |
| A-48 | Cl | NH | —O—CH₂—O— | | H | (A) | 1 | 3-CH₂OH | H |
| A-49 | CH₃ | NH | —O—CH₂—O— | | H | (A) | 1 | 3-CH₂OH | H |
| A-50 | OCH₃ | NH | —O—CH₂—O— | | H | (A) | 1 | 3-CH₂OH | H |
| A-51 | 1-morpholinyl | NH | —O—CH₂—O— | | H | (A) | 1 | 3-CH₂OH | H |
| A-52 | 1-pyrrolidinyl | NH | —O—CH₂—O— | | H | (A) | 1 | 3-CH₂OH | H |
| A-53 | NH-propargyl | NH | —O—CH₂—O— | | H | (A) | 1 | 3-CH₂OH | H |
| A-54 | Cl | NCH₃ | —O—CH₂—O— | | H | (A) | 1 | 3-CH₂OH | H |
| A-55 | Cl | O | —O—CH₂—O— | | H | (A) | 1 | 3-CH₂OH | H |
| A-56 | Cl | S | —O—CH₂—O— | | H | (A) | 1 | 3-CH₂OH | H |
| A-57 | Cl | CH₂ | —O—CH₂—O— | | H | (A) | 1 | 3-CH₂OH | H |
| A-58 | Cl | bond | —O—CH₂—O— | | H | (A) | 1 | 3-CH₂OH | H |
| A-59 | Cl | NH | —O—CH₂—O— | | H | (A) | 1 | 4-CH₂OH | H |
| A-60 | Cl | NH | —O—CH₂—O— | | H | (A) | 0 | 3-OH | H |
| A-61 | Cl | NH | CH₃ | H | H | (A) | 0 | 3-OH | H |
| A-62 | Cl | NH | Cl | H | H | (A) | 0 | 3-OH | H |
| A-63 | Cl | NH | OCH₃ | H | H | (A) | 0 | 3-OH | H |
| A-64 | Cl | NH | H | OCH₃ | H | (A) | 0 | 3-OH | H |
| A-65 | Cl | NH | H | OC₂H₅ | H | (A) | 0 | 3-OH | H |
| A-66 | Cl | NH | H | 1-morpholinyl | H | (A) | 0 | 3-OH | H |
| A-68 | Cl | NH | CH₃ | CH₃ | H | (A) | 0 | 3-OH | H |
| A-69 | Cl | NH | F | OCH₃ | H | (A) | 0 | 3-OH | H |
| A-70 | Cl | NH | -phenyl- | | H | (A) | 0 | 3-OH | H |
| A-71 | Cl | NH | —O—CH₂—O— | | H | (A) | 0 | 3-CH₂OH | H |

| nr | R₁ | X | R₂ | R₃ | R₄ | Y | R₇ | R₈ | R₉ | R₁₀ | stereo |
|---|---|---|---|---|---|---|---|---|---|---|---|
| B-1 | Cl | NH | H | H | H | (B) | CH₃ | H | H | H | 1S,2R |
| B-2 | Cl | NH | H | H | H | (B) | CH₃ | H | H | H | 1R,2S |
| B-3 | Cl | NCH₃ | H | H | H | (B) | CH₃ | H | H | H | 1S,2R |
| B-4 | Cl | O | H | H | H | (B) | CH₃ | H | H | H | 1S,2R |

-continued

| Nr | R$_1$ | X | R$_2$ | R$_3$ | R$_4$ | Y | R$_8$ | R$_9$ | R$_{10}$ | R$_{11}$ | Z |
|---|---|---|---|---|---|---|---|---|---|---|---|
| B-5 | Cl | CH$_2$ | H | H | H | (B) | CH$_3$ | H | H | H | 1S,2R |
| B-6 | Cl | S | H | H | H | (B) | CH$_3$ | H | H | H | 1S,2R |
| B-7 | Cl | bond | H | H | H | (B) | CH$_3$ | H | H | H | 1S,2R |
| B-8 | Cl | NH | H | H | H | (B) | CH$_3$ | H | H | CH$_3$ | 1R,2S |
| B-9 | Cl | NH | OCH$_3$ | H | H | (B) | CH$_3$ | H | H | H | 1S,2R |
| B-10 | Cl | NH | OCH$_3$ | H | H | (B) | CH$_3$ | H | H | H | 1R,2S |
| B-11 | Cl | NH | OCH$_3$ | H | H | (B) | CH$_3$ | H | H | CH$_3$ | 1R,2R |
| B-12 | Cl | NH | OCH$_3$ | H | H | (B) | CH$_2$CH$_3$ | H | H | H | 1S,2R |
| B-13 | Cl | NH | OCH$_3$ | H | H | (B) | (CH$_2$)$_2$CH$_3$ | H | H | H | 1S,2R |
| B-14 | Cl | NH | OCH$_3$ | H | H | (B) | CH$_2$-phenyl | H | H | H | 1S,2R |
| B-15 | Cl | NH | OCH$_3$ | H | H | (B) | CH$_2$OH | H | H | H | 1S,2R |
| B-16 | Cl | NH | OCH$_2$CH$_3$ | H | H | (B) | CH$_3$ | H | H | H | 1S,2R |
| B-17 | Cl | NH | OCH$_2$CH$_3$ | H | H | (B) | CH$_3$ | H | H | CH$_3$ | 1R,2R |
| B-18 | Cl | NH | CH$_3$ | H | H | (B) | CH$_3$ | H | H | H | 1S,2R |
| B-19 | Cl | NH | Cl | H | H | (B) | CH$_3$ | H | H | H | 1S,2R |
| B-20 | Cl | NH | Cl | H | H | (B) | CH$_3$ | H | H | CH$_3$ | 1R,2R |
| B-21 | Cl | NH | CH(OH)CH$_3$ | H | H | (B) | CH$_3$ | H | H | H | 1S,2R |
| B-22 | Cl | NH | CH(OH)CH$_3$ | H | H | (B) | CH$_3$ | H | H | CH$_3$ | 1R,2R |
| B-23 | Cl | NH | O-phenyl | H | H | (B) | CH$_3$ | H | H | H | 1S,2R |
| B-24 | Cl | NH | O-phenyl | H | H | (B) | CH$_3$ | H | H | CH$_3$ | 1R,2R |
| B-25 | Cl | NH | H | OCH$_3$ | H | (B) | CH$_3$ | H | H | H | 1S,2R |
| B-26 | Cl | NH | H | OCH$_3$ | H | (B) | CH$_3$ | H | H | H | 1R,2S |
| B-27 | Cl | NH | H | OCH$_3$ | H | (B) | CH$_3$ | H | H | CH$_3$ | 1R,2R |
| B-28 | Cl | NH | H | OCH$_2$CH$_3$ | H | (B) | CH$_3$ | H | H | H | 1S,2R |
| B-29 | Cl | NH | H | 1-morpholinyl | H | (B) | CH$_3$ | H | H | H | 1S,2R |
| B-30 | Cl | NH | H | CH$_3$ | H | (B) | CH$_3$ | H | H | H | 1S,2R |
| B-31 | Cl | NH | H | CF$_3$ | H | (B) | CH$_3$ | H | H | H | 1S,2R |
| B-32 | Cl | NH | H | O-phenyl | H | (B) | CH$_3$ | H | H | H | 1S,2R |
| B-33 | Cl | NH | H | O-phenyl | H | (B) | CH$_3$ | H | H | CH$_3$ | 1R,2R |
| B-34 | Cl | NH | H | (CH$_2$)$_2$OH | H | (B) | CH$_3$ | H | H | CH$_3$ | 1R,2R |
| B-35 | Cl | NH | F | CH$_3$ | H | (B) | CH$_3$ | H | H | H | 1S,2R |
| B-36 | Cl | NH | F | OCH$_3$ | H | (B) | CH$_3$ | H | H | H | 1S,2R |
| B-37 | Cl | NH | F | OCH$_3$ | H | (B) | CH$_3$ | H | H | CH$_3$ | 1R,2R |
| B-38 | Cl | NH | F | OCH$_3$ | H | (B) | CH$_3$ | H | H | CH$_3$ | 1R,2S |
| B-39 | Cl | NH | OCH$_3$ | H | CF$_3$ | (B) | CH$_3$ | H | H | H | 1S,2R |
| B-40 | Cl | NH | OCH$_3$ | H | OCH$_3$ | (B) | CH$_3$ | H | H | H | 1S,2R |
| B-41 | Cl | NH | OCH$_3$ | H | OCH$_3$ | (B) | CH$_3$ | H | H | CH$_3$ | 1R,2R |
| B-42 | Cl | NH | CH$_3$ | CH$_3$ | H | (B) | CH$_3$ | H | H | H | 1S,2R |
| B-43 | Cl | NH | -phenyl- | H | H | (B) | CH$_3$ | H | H | H | 1S,2R |
| B-44 | Cl | NH | —O—CH$_2$—O— | | H | (B) | CH$_3$ | H | H | H | 1S,2R |
| B-45 | Cl | NH | —O—CH$_2$—O— | | H | (B) | CH$_3$ | H | H | H | 1R,2S |
| B-46 | Cl | NH | —O—CH$_2$—O— | | H | (B) | CH$_3$ | H | H | CH$_3$ | 1S,2R |
| B-47 | Cl | NH | —O—CH$_2$—O— | | H | (B) | CH$_3$ | H | H | CH$_3$ | 1S,2S |
| B-48 | Cl | NH | —O—CH$_2$—O— | | H | (B) | CH$_3$ | H | H | CH$_3$ | 1R,2S |
| B-49 | Cl | NH | —O—CH$_2$—O— | | H | (B) | CH$_3$ | H | H | CH$_3$ | 1R,2R |
| B-50 | Cl | NCH$_3$ | —O—CH$_2$—O— | | H | (B) | CH$_3$ | H | H | H | 1S,2R |
| B-51 | Cl | O | —O—CH$_2$—O— | | H | (B) | CH$_3$ | H | H | H | 1S,2R |
| B-52 | Cl | S | —O—CH$_2$—O— | | H | (B) | CH$_3$ | H | H | H | 1S,2R |
| B-53 | Cl | CH$_2$ | —O—CH$_2$—O— | | H | (B) | CH$_3$ | H | H | H | 1S,2R |
| B-54 | Cl | bond | —O—CH$_2$—O— | | H | (B) | CH$_3$ | H | H | H | 1S,2R |
| B-55 | Cl | NH | —O—CH$_2$—O— | | H | (B) | CH$_3$ | 3-OH | H | H | 1R,2S |
| B-56 | Cl | NH | —O—CH$_2$—O— | | H | (B) | CH$_3$ | 4-OH | H | H | 1S,2R |
| B-57 | Cl | NH | —O—CH$_2$—O— | | H | (B) | CH$_3$ | 3-OH | 4-OH | H | 1R,2S |
| B-58 | Cl | NH | —O—CH$_2$—O— | | H | (B) | CH$_3$ | 2-OCH$_3$ | 5-OCH$_3$ | H | racemic |
| B-59 | NH$_2$ | NH | —O—CH$_2$—O— | | H | (B) | CH$_3$ | H | H | H | 1R,2S |
| B-60 | N(CH$_3$)$_2$ | NH | —O—CH$_2$—O— | | H | (B) | CH$_3$ | H | H | H | 1R,2S |
| B-61 | 1-pyrrolidinyl | NH | —O—CH$_2$—O— | | H | (B) | CH$_3$ | H | H | H | 1S,2R |
| B-62 | 1-morpholinyl | NH | —O—CH$_2$—O— | | H | (B) | CH$_3$ | H | H | H | 1S,2R |
| B-63 | 1-piperidinyl | NH | —O—CH$_2$—O— | | H | (B) | CH$_3$ | H | H | H | 1S,2R |
| B-64 | NH-propargyl | NH | —O—CH$_2$—O— | | H | (B) | CH$_3$ | H | H | H | 1S,2R |
| B-65 | N(CH$_3$)pro-propargyl | NH | —O—CH$_2$—O— | | H | (B) | CH$_3$ | H | H | H | 1S,2R |
| B-66 | CH$_3$ | NH | —O—CH$_2$—O— | | H | (B) | CH$_3$ | H | H | H | 1S,2R |
| B-67 | OCH$_3$ | NH | —O—CH$_2$—O— | | H | (B) | CH$_3$ | H | H | H | 1S,2R |

| Nr | R$_1$ | X | R$_2$ | R$_3$ | R$_4$ | Y | R$_8$ | R$_9$ | R$_{10}$ | R$_{11}$ | Z |
|---|---|---|---|---|---|---|---|---|---|---|---|
| C-1 | Cl | NH | —O—CH$_2$O— | | H | (C) | H | H | H | H | O |
| C-2 | Cl | NH | —O—CH$_2$O— | | H | (C) | H | H | H | CH$_3$ | O |
| C-3 | CH$_3$ | NH | —O—CH$_2$O— | | H | (C) | H | H | H | CH$_3$ | O |
| C-4 | OCH$_3$ | NH | —O—CH$_2$O— | | H | (C) | H | H | H | CH$_3$ | O |
| C-5 | Cl | NH | OCH$_3$ | H | H | (C) | H | H | H | CH$_3$ | O |
| C-6 | Cl | NH | H | OCH$_3$ | H | (C) | H | H | H | CH$_3$ | O |
| C-7 | Cl | NH | —O—CH$_2$O— | | H | (C) | H | H | H | CH$_3$ | N—OH |
| C-8 | Cl | NH | —O—CH$_2$O— | | H | (C) | H | H | H | CH$_3$ | N—OCH$_3$ |
| C-9 | Cl | NH | —O—CH$_2$O— | | H | (C) | H | H | H | H | N—OH |
| C-10 | Cl | NH | OCH$_3$ | H | H | (C) | H | H | H | H | N—OH |
| C-11 | Cl | NH | H | OCH$_3$ | H | (C) | H | H | H | H | N—OH |

EXAMPLES OF PRODRUGS

To illustrate the concept 'prodrugs' the following compounds with the general formula (10) have been prepared:

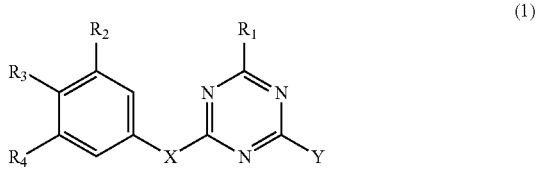
(10)

| example | R-group |
|---------|---------|
| Pro-1 | propionyl |
| Pro-2 | pivaloyl |
| Pro-3 | nicotinoyl |
| Pro-4 | N-acetyl-isonipecotyl |
| Pro-5 | methoxyacetyl |
| Pro-6 | acethoxyacetyl |
| Pro-7 | nonaoyl |

Prodrugs having formula (10) have no affinity for human adenosine-A3 receptors, but after hydrolysis they generate the compound with formula (9) (see above) which is highly active.

The invention claimed is:

1. A compound of the formula (1):

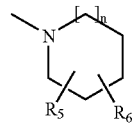

wherein:
$R_1$ represents halogen, alkyl(1-3C), O-alkyl(1-3C), $CF_3$, $NH_2$, N-(di)-alkyl(1-3C), N-(di)-alkenyl(1-3C), N-(di)-alkynyl(1-3C), N-alkyl(1-3C)alkenyl(1-3C), N-alkyl(1-3C)alkynyl(1-3C), N-alkenyl(1-3C)alkynyl(1-3C) or an optionally substituted cyclic amine containing from 2 to 8 carbons in the ring;

$R_2$, $R_3$ and $R_4$ independently represent H, halogen, alkyl(1-3C), $CF_3$, OH, O-alkyl(1-3C), phenoxy, hydroxyalkyl(1-3C), alkoxy(1-2C)-alkyl(1-2C), phenyl, N-(di)-alkyl(1-3C), 1-morpholinyl, 1-piperidinyl, 1-piperazinyl, $OCF_3$, $SCH_3$, $SOCH_3$, $SO_2CH_3$ or $R_2$ and $R_3$ together with the phenyl ring to which they are attached, represent an optionally substituted benzofuran, dihydrobenzofuran, benzodioxane, benzodioxolane or naphthalene ring system, X represents NH, N-alkyl(1-3C), $CH_2$, O, S;

Y represents a group of the general formula (A), (B) or (C):

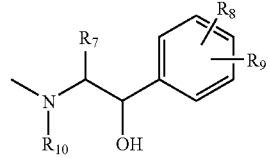
(A)

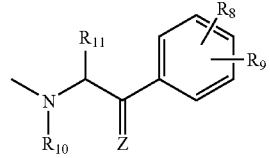
(B)

(C)

in which:
$R_5$ is either OH or $CH_2OH$;
$R_6$ represents H, alkyl(1-3C), phenyl, $NH_2$, N-(di)-alkyl(1-3C), OH, O-alkyl(1-3C) or hydroxyalkyl(1-2C);
n has the value of 0, 1 or 2;
$R_7$ represents alkyl(1-3C), benzyl, hydroxyalkyl(1-2C) or methoxyalkyl(1-2C),
$R_8$ and $R_9$ independently represent H, halogen, alkyl(1-3C), $CF_3$, OH, O-alkyl(1-3C), N-(di)-alkyl(1-3C), 1-morpholinyl, 1-piperidinyl, 1-piperazinyl, $OCF_3$, $SCH_3$, $SOCH_3$, or $SO_2CH_3$;
$R_{10}$ represents H or alkyl(1-3C);
$R_{11}$ represents H, alkyl(1-3C), benzyl, hydroxyalkyl(1-2C) or methoxyalkyl(1-2C); and
Z represents NOH, NOalkyl(1-3C), O or S;
a compound having formula (1) in which the substituents on one or more asymmetrical carbon atoms are in either the R-configuration or the S-configuration, a stereoisomer of a compound of formula (1), a prodrug of a compound of formula (1), or a pharmacologically acceptable salt of any of the foregoing.

2. The compound of the formula (1) as claimed in claim 1 wherein $R_1$ represents halogen, alkyl(1-3C), O-alkyl(1-3C), $CF_3$, $NH_2$ or N-(di)-alkyl(1-3C); $R_2$, $R_3$ and $R_4$ independently represent H, halogen, alkyl(1-3C), $CF_3$, OH, O-alkyl(1-3C), phenyl, N-(di)-alkyl(1-3C), 1-morpholinyl, 1-piperidinyl, 1-piperazinyl, $OCF_3$, $SCH_3$, $SOCH_3$, $SO_2CH_3$, or $R_2$ and $R_3$ together with the phenyl ring to which they are attached, represent a benzofuran, benzodioxane, or benzodioxolane ring system, X represents NH, N-alkyl(1-3C), $CH_2$, O, or S, Y represents a group of the general formula (A) or (B), in which $R_5$ is either OH or $CH_2OH$; $R_6$ represents H, alkyl(1-3C), phenyl, $NH_2$, N-(di)-alkyl(1-3C), OH, O-alkyl(1-3C) or hydroxyalkyl (1-2C); n has the value of 0, 1 or 2; $R_7$ represents alkyl(1-3C), benzyl or hydroxyalkyl(1-2C); $R_8$ and $R_9$ independently represent H, halogen, alkyl(1-3C), $CF_3$, OH, O-alkyl(1-3C), N-(di)-alkyl(1-3C), 1-morpholinyl, 1-piperidinyl, 1-piperazinyl, $OCF_3$, $SCH_3$, $SOCH_3$, or $SO_2CH_3$; and $R_{10}$ represents H.

3. The compound of the formula (1) as claimed in claim 1 wherein Y is a group of the formula (A).

4. The compound of the formula (1) as claimed in claim 2 wherein Y is a group of the formula (A).

5. The compound of the formula (1) as claimed in claim 1 wherein Y is a group of the formula (B).

6. The compound of the formula (1) as claimed in claim 2 wherein Y is a group of the formula (B).

7. The compound of the formula (1) as claimed in claim 1 wherein Y is a group of the formula (C).

8. The compound of the formula (1) as claimed in claim 1 wherein $R_1$ is Cl, $R_2$ is H, X is NH, $R_6$ is H, n is 1, Z is O, and $R_{10}$ is H.

9. The compound of the formula (1) as claimed in claim 1 wherein $R_1$ is Cl, $R_2$ is H, X is NH, $R_5$ is 3—$CH_2OH$, $R_6$ is H, n is 1, $R_7$ is $CH_3$; $R_8$ is H; $R_9$ is H, Z is O, $R_{10}$ is H, and $R_{11}$ is $CH_3$.

10. The compound as claimed in claim 1 having formula (8) or an enantiomer thereof:

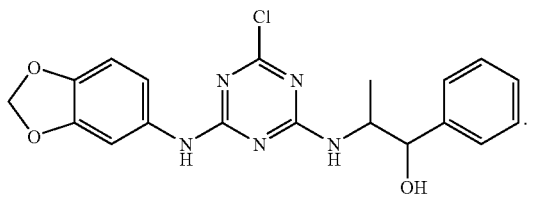

(8)

11. The compound as claimed in claim 1 having formula (9):

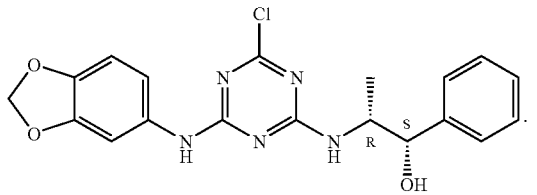

(9)

12. A pharmaceutical composition comprising a pharmacologically active amount of one or more compounds as claimed in claim 1, and one or more pharmaceutically acceptable carriers.

13. A method of treating at least one inflammatory disease involving one or more adenosine-$A_3$ receptors, or that can be treated via manipulation of one or more adenosine-$A_3$ receptors, wherein the at least one inflammatory disease is chosen from arthritis, multiple sclerosis, asthma, and psoriasis, in a human patient comprising administering to the patient an effective amount of one or more compounds of the formula (1):

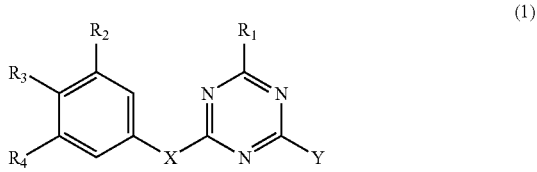

(1)

wherein:
R$_1$ represents halogen, alkyl(1-3C), O-alkyl(1-3C), CF$_3$, NH$_2$, N-(di)-alkyl(1-3C), N-(di)-alkenyl(1-3C), N-(di)-alkynyl(1-3C), N-alkyl(1-3C)alkenyl(1-3C), N-alkyl(1-3C)alkynyl(1-3C), N-alkenyl(1-3C)alkynyl(1-3C) or an optionally substituted cyclic amine containing from 2 to 8 carbons in the ring;

R$_2$, R$_3$ and R$_4$ independently represent H, halogen, alkyl (1-3C), CF$_3$, OH, O-alkyl(1-3C), phenoxy, hydroxyalkyl(1-3C), alkoxy(1-2C)-alkyl(1-2C), phenyl, N-(di)-alkyl(1-3C), 1-morpholinyl, 1-piperidinyl, 1-piperazinyl, OCF$_3$, SCH$_3$, SOCH$_3$, SO$_2$CH$_3$ or R$_2$ and R$_3$ together with the phenyl ring to which they are attached, represent an optionally substituted benzofuran, dihydrobenzofuran, benzodioxane, benzodioxolane or naphthalene ring system;

X represents NH, N-alkyl(1-3C), CH$_2$, O, S or a carbon-carbon bond;

Y represents a group of the general formula (A), (B) or (C):

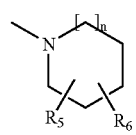

(A)

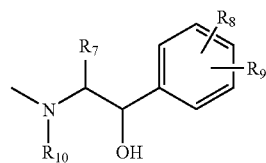

(B)

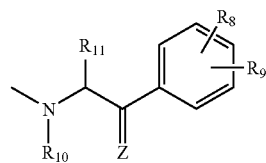

(C)

in which:
R$_5$ is either OH or CH$_2$OH;
R$_6$ represents H, alkyl(1-3C), phenyl, NH$_2$, N-(di)-alkyl (1-3C), OH, O-alkyl(1-3C) or hydroxyalkyl(1-2C);
n has the value of 0, 1 or 2;
R$_7$ represents alkyl(1-3C), benzyl, hydroxyalkyl(1-2C) or methoxyalkyl(1-2C);
R$_8$ and R$_9$ independently represent H, halogen, alkyl(1-3C), CF$_3$, OH, O-alkyl(1-3C), N-(di)-alkyl(1-3C), 1-morpholinyl, 1-piperidinyl, 1-piperazinyl, OCF$_3$, SCH$_3$, SOCH$_3$, or SO$_2$CH$_3$;
R$_{10}$ represents H or alkyl(1-3C);
R$_{11}$ represents H, alkyl(1-3C), benzyl, hydroxyalkyl(1-2C) or methoxyalkyl(1-2C); and
Z represents NOH, NOalkyl(1-3C), O or S;
one or more compounds having formula (1) in which the substituents on one or more asymmetrical carbon atoms are in either the R-configuration or the S-configuration, one or more stereoisomers of a compound of formula (1), one or more prodrugs of a compound of formula (1), one or more pharmacologically acceptable salts of any of the foregoing, or a combination of two or more of any of the foregoing.

14. A method of treating Parkinson's disease in a human patient comprising administering to the patient an effective amount of one or more compounds of the formula (1):

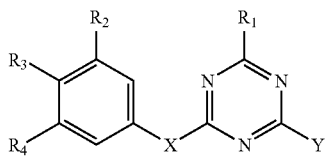
(1)

wherein:

- $R_1$ represents halogen, alkyl(1-3C), O-alkyl(1-3C), $CF_3$, $NH_2$, N-(di)-alkyl(1-3C), N-(di)-alkenyl(1-3C), N-(di)-alkynyl(1-3C), N-alkyl(1-3C)alkenyl(1-3C), N-alkyl(1-3C)alkynyl(1-3C), N-alkenyl(1-3C)alkynyl(1-3C) or an optionally substituted cyclic amine containing from 2 to 8 carbons in the ring;
- $R_2$, $R_3$ and $R_4$ independently represent H, halogen, alkyl(1-3C), $CF_3$, OH, O-alkyl(1-3C), phenoxy, hydroxyalkyl(1-3C), alkoxy(1-2C)-alkyl(1-2C), phenyl, N-(di)-alkyl(1-3C), 1-morpholinyl, 1-piperidinyl, 1-piperazinyl, $OCF_3$, $SCH_3$, $SOCH_3$, $SO_2CH_3$ or $R_2$ and $R_3$ together with the phenyl ring to which they are attached, represent an optionally substituted benzofuran, dihydrobenzofuran, benzodioxane, benzodioxolane or naphthalene ring system;
- X represents NH, N-alkyl(1-3C), $CH_2$, O, S or a carbon-carbon bond;
- Y represents a group of the general formula (A), (B) or (C):

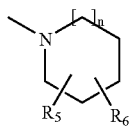
(A)

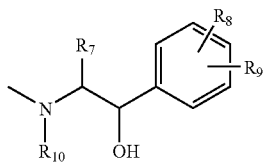
(B)

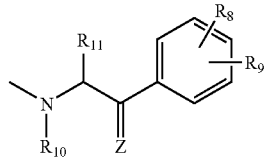
(C)

in which:

- $R_5$ is either OH or $CH_2OH$;
- $R_6$ represents H, alkyl(1-3C), phenyl, $NH_2$, N-(di)-alkyl(1-3C), OH, O-alkyl(1-3C) or hydroxyalkyl(1-2C);
- n has the value of 0, 1 or 2;
- $R_7$ represents alkyl(1-3C), benzyl, hydroxyalkyl(1-2C) or methoxyalkyl(1-2C);
- $R_8$ and $R_9$ independently represent H, halogen, alkyl(1-3C), $CF_3$, OH, O-alkyl(1-3C), N-(di)-alkyl(1-3C), 1-morpholinyl, 1-piperidinyl, 1-piperazinyl, $OCF_3$, $SCH_3$, $SOCH_3$, or $SO_2CH_3$;
- $R_{10}$ represents H or alkyl(1-3C);
- $R_{11}$ represents H, alkyl(1-3C), benzyl, hydroxyalkyl(1-2C) or methoxyalkyl(1-2C); and
- Z represents NOH, NOalkyl(1-3C), O or S;
- one or more compounds having formula (1) in which the substituents on one or more asymmetrical carbon atoms are in either the R-configuration or the S-configuration, one or more stereoisomers of a compound of formula (1), one or more prodrugs of a compound of formula (1), one or more pharmacologically acceptable salts of any of the foregoing, or a combination of two or more of any of the foregoing.

\* \* \* \* \*